United States Patent
Satou (10) Patent No.: US 11,963,852 B2
(45) Date of Patent: Apr. 23, 2024

(54) ABSORBENT MATERIAL MANUFACTURING DEVICE

(71) Applicant: ZUIKO CORPORATION, Settu (JP)

(72) Inventor: Hitoshi Satou, Settu (JP)

(73) Assignee: ZUIKO CORPORATION, Settu (JP)

( * ) Notice: Subject to any disclaimer, the term of this patent is extended or adjusted under 35 U.S.C. 154(b) by 1022 days.

(21) Appl. No.: 16/762,378

(22) PCT Filed: Oct. 26, 2018

(86) PCT No.: PCT/JP2018/040005
§ 371 (c)(1),
(2) Date: May 7, 2020

(87) PCT Pub. No.: WO2019/097988
PCT Pub. Date: May 23, 2019

(65) Prior Publication Data
US 2020/0352793 A1  Nov. 12, 2020

(30) Foreign Application Priority Data
Nov. 15, 2017  (JP) .................................. 2017-220449

(51) Int. Cl.
*B05B 7/14*  (2006.01)
*A61F 13/15*  (2006.01)
(Continued)

(52) U.S. Cl.
CPC .. *A61F 13/15642* (2013.01); *A61F 13/15658* (2013.01); *B01J 20/26* (2013.01);
(Continued)

(58) Field of Classification Search
USPC ...... 118/308, 310, 311, 301; 425/80.1, 81.1, 425/82.1, 83.1, 72.1; 156/276
See application file for complete search history.

(56) References Cited

U.S. PATENT DOCUMENTS

2013/0062802 A1*  3/2013  Goda ................ A61F 13/15658
                                                                425/140
2014/0027943 A1*  1/2014  Hoshika ............ A61F 13/15658
                                                                425/449

FOREIGN PATENT DOCUMENTS

EP     1253231 A2    10/2002
JP     H10-137286 A   5/1998
(Continued)

OTHER PUBLICATIONS

English Translation JP2016-515455A (Year: 2016).*
(Continued)

*Primary Examiner* — Yewebdar T Tadesse
(74) *Attorney, Agent, or Firm* — Manabu Kanesaka (57) ABSTRACT

In a method and device for manufacturing an absorbent material, the degree of freedom in design can be increased by expanding a modifiable distribution pattern of an SAP and broadening the range in which the performance of the absorbent material can be modified. Pulverized pulp is suctioned in a predetermined pattern to form a pulp layer in which the pulp is fiber-laminated. A first distribution opening through which a first distribution device discharges a first SAP and a second distribution opening through which a second distribution opening discharges a second SAP are provided facing the pulp layer, and the first and second SAPs are distributed onto the pulp layer through the first and second distribution openings while moving the pulp layer relative to the first and second distribution openings. The first and second distribution devices can control the discharge amounts of the first SAP and the second SAP, respectively.

5 Claims, 5 Drawing Sheets

(51) Int. Cl.
*B01J 20/26* (2006.01)
*B05B 12/16* (2018.01)

(52) U.S. Cl.
CPC ............... *B05B 7/14* (2013.01); *B05B 12/16* (2018.02); *A61F 2013/15926* (2013.01)

(56) References Cited

FOREIGN PATENT DOCUMENTS

| | | |
|---|---|---|
| JP | 3462232 B | 11/2003 |
| JP | 2015-019909 A | 2/2015 |
| JP | 2016515455 A * | 5/2016 |
| WO | 2005/061120 A1 | 7/2005 |
| WO | 2007/111873 A2 | 10/2007 |

OTHER PUBLICATIONS

Europe Patent Office, "Search Report for European Patent Application No. 18877559.7," dated Aug. 18, 2021.
PCT/ISA/210, "International Search Report for International Application No. PCT/JP2018/040005," dated Dec. 11, 2018.

* cited by examiner

ABSORBENT MATERIAL MANUFACTURING DEVICE

RELATED APPLICATIONS

The present application is National Phase of International Application No. PCT/JP2018/040005 filed Oct. 26, 2018, and claim a priority from Japanese Application No. 2017-220449, filed Nov. 15, 2017, the disclosures of which are hereby incorporated by reference herein in its entirety.

TECHNICAL FIELD

The present invention relates to a method and device for manufacturing an absorbent material, and more specifically, relates to a method for manufacturing an absorbent material including a pulp layer.

BACKGROUND ART

An absorbent material including a pulp layer in which pulverized pulp is fiber-laminated and a superabsorbent polymer (hereinafter, referred to as "SAP") layer (hereinafter, referred to as "SAP layer") is used for absorbent material cores for disposable diapers and women's sanitary products, and the like.

Figure 6:
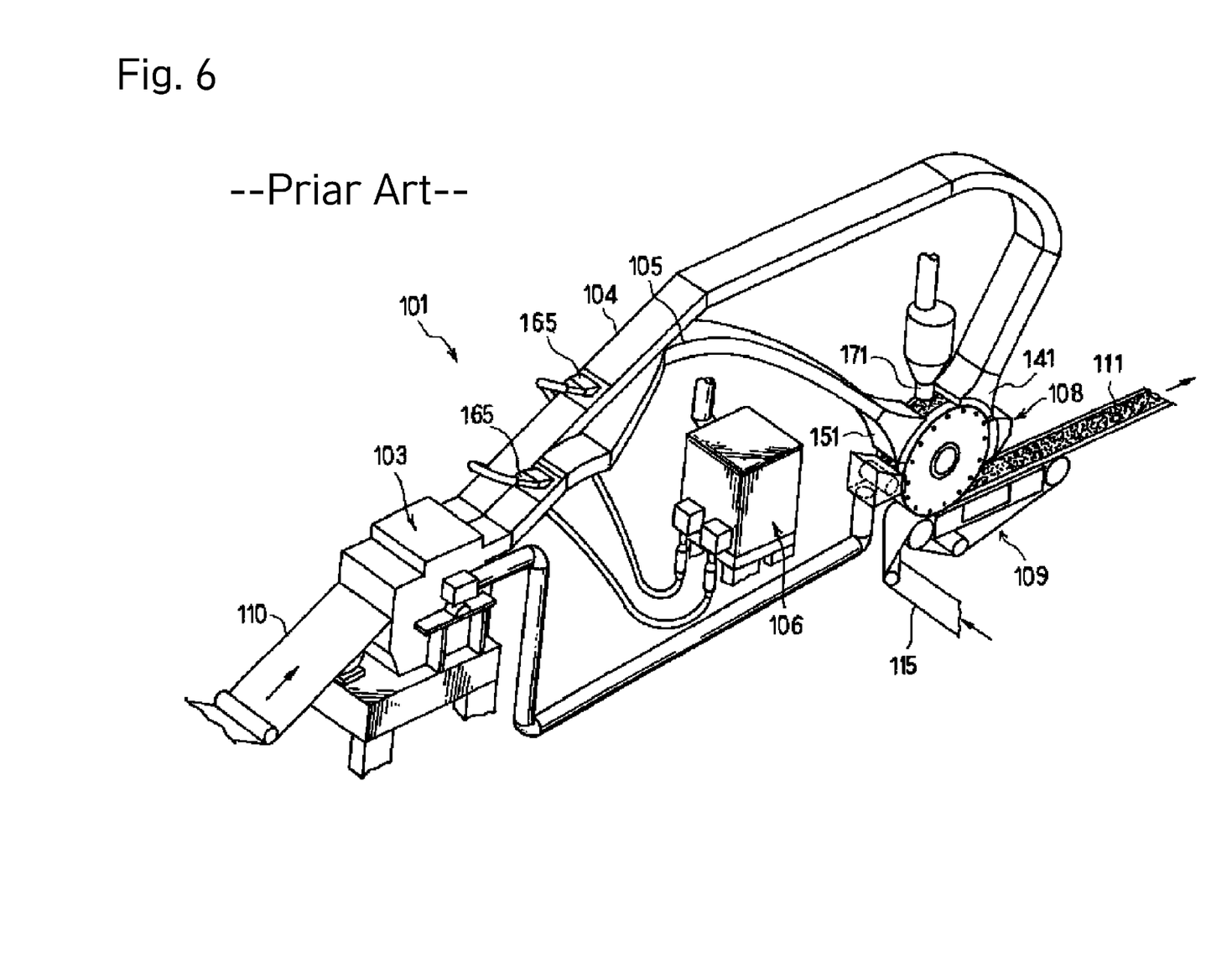
FIG. 6 is a perspective view of the absorbent material manufacturing device (conventional example).

Such an absorbent material is manufactured, for example, by using an absorbent material manufacturing device 101 shown in the perspective view of FIG. 6. As shown in FIG. 6, this device 101 pulverizes a sheet-like pulp material 110 with a pulverization device 103. The pulverized pulp is conveyed inside ducts 104 and 105. The ducts 104 and 105 are disposed so that respective open parts 141 and 151 face the air-permeable outer peripheral surface of a rotary drum 108. Between the two open parts 141 and 151, a distribution opening 171 that supplies the SAP is disposed facing the air-permeable outer peripheral surface of the rotary drum 108. Although not shown, suction chambers facing the open parts 141 and 151 and the distribution opening 171, respectively, are provided inside the rotary drum 108.

After discharged through the open part 141 of one duct 104, the pulp pulverized by the pulverization device 103 is suctioned in a predetermined pattern and fiber-laminated on the outer peripheral surface of the rotary drum 108 to form a pulp layer. The SAP is distributed thereonto through the distribution opening 171 to form an SAP layer. The pulp pulverized by the pulverization device 103 is discharged through the open part 151 of the other duct 105, and suctioned in a predetermined pattern and fiber-laminated on the SAP layer to form a pulp layer. Thereby, an absorbent material 111 in which the SAP layer is sandwiched between the pulp layers is manufactured.

By blowing air from the inside of the rotary drum 108, the absorbent material 111 on the outer peripheral surface of the rotary drum 108 is transferred onto an air-permeable pasteboard 115 conveyed by a vacuum conveyer 109, and conveyed together with the pasteboard 115.

Further, this device 101 is capable of dispersing the SAP to the pulp layer of the absorbent material 111 by jetting the SAP from the tip of a nozzle 165 inserted in the ducts 104 and 105. To the nozzle 165 and the distribution opening 171, the SAP is supplied from a single distribution device 106 (for example, see Patent Literature 1).

CITATION LIST

Patent Literature

[Patent Literature 1] Japanese Patent No. 3462232

SUMMARY OF THE INVENTION

Problem to be Solved by the Invention

When the SAP is distributed in order to form the SAP layer, if the distribution pattern of the SAP is modified, the absorption performance of the absorbent material can be modified.

According to the above-described conventional technology, since one kind of SAP is distributed through one distribution opening 171 by using the single distribution device 106, the distribution pattern of the SAP is limited. For this reason, the range is small in which the absorption performance of the absorbent material can be modified by modifying the distribution pattern of the SAP.

In view of such circumstances, a problem to be solved by the present invention is to provide a method and device for manufacturing an absorbent material wherein the degree of freedom in performance design can be increased by expanding a modifiable distribution pattern of the SAP and broadening the range in which the performance of the absorbent material can be modified.

Means for Solving the Problem

To solve the above-mentioned problem, the present invention provides an absorbent material manufacturing method structured as follows:

The absorbent material manufacturing method is provided with: (i) a first step in which a pulp pulverized and conveyed by a duct is suctioned in a predetermined pattern to form a pulp layer in which the pulp is fiber-laminated; and (ii) a second step in which a first distribution opening through which a first distribution device discharges a first SAP and a second distribution opening through which a second distribution device discharges a second SAP are provided facing the pulp layer, and the first SAP discharged through the first distribution opening is distributed onto the pulp layer and the second SAP discharged through the second distribution opening is distributed onto the pulp layer while moving the pulp layer relative to the first distribution opening and the second distribution opening. In the second step, the first distribution device can control the discharge amount of the first SAP, and the second distribution device can control the discharge amount of the second SAP.

By the above-described method, an absorbent material including the pulp layer, the first SAP and the second SAP can be manufactured.

According to the above-described method, by using the first and second distribution devices, the distribution amount of the first SAP and the distribution amount of the second SAP can be controlled. For this reason, by changing the combination of the distribution amounts of the first SAP and the second SAP, the performance of the absorbent material can be variously modified. Moreover, by changing either one or both of the distribution amount of the first SAP and the distribution amount of the second SAP while moving the pulp layer relative to the first distribution opening and the second distribution opening, an absorbent material can be easily manufactured in which the densities of the SAPs differ in the direction of the relative movement of the pulp layer.

That is, by using a plurality of distribution devices that discharge different SAPs and making it possible to control the distribution amounts of the SAPs, the modifiable distribution pattern of the SAPs can be expanded compared with a case where a single distribution device is used. For this reason, the range in which the performance of the absorbent material can be modified is broadened, so that the degree of freedom in performance design is increased.

Preferably, in the first step, a sheet with air permeability is conveyed along an outer peripheral surface, with air permeability, of a rotating drum and the pulp is suctioned in the predetermined pattern onto the sheet to form the pulp layer.

In this case, the absorbent material including the sheet can be easily taken out from the outer peripheral surface of the drum.

Preferably, the absorbent material manufacturing method is further provided with (iii) a third step in which pulverized pulp the same as or different from the above pulp is suctioned in a pattern the same as or different from the predetermined pattern and fiber-laminated on the pulp layer in which the first SAP and the second SAP are distributed.

In this case, an absorbent material in which the SAP layer is disposed between the pulp layers can be manufactured.

Preferably, in the second step, the first SAP and the second SAP having different performances are distributed.

In this case, according to the combination of the performances of the SAPs, the range in which the performance of the absorbent material can be modified is further broadened, so that the degree of freedom in performance choice can be further increased.

Moreover, to solve the above-described problem, the present invention provides an absorbent material manufacturing method structured as follow:

The absorbent material manufacturing method is provided with: (i) a first step in which a first distribution opening through which a first distribution device discharges a first SAP and a second distribution opening through which a second distribution device discharges a second SAP are provided facing a sheet, and the first SAP discharged through the first distribution opening is distributed onto the sheet and the second SAP discharged through the second distribution opening is distributed onto the sheet while moving the sheet relative to the first distribution opening and the second distribution opening; and (ii) a second step in which onto the sheet where the first SAP and the second SAP are distributed, a pulp pulverized and conveyed by a duct is suctioned in a predetermined pattern to form a pulp layer, in which the pulp is fiber-laminated, so that the pulp layer covers the first SAP and the second SAP distributed onto the sheet. In the first step, the first distribution device can control the discharge amount of the first SAP, and the second distribution device can control the discharge amount of the second SAP.

According to the above-described method, by using a plurality of distribution devices that discharge different SAPs and making it possible to control the distribution amounts of the SAPs, the modifiable distribution pattern of the SAPs is expanded compared with a case where a single distribution device is used. For this reason, the range in which the performance of the absorbent material can be modified is broadened, so that the degree of freedom in performance design is increased.

Moreover, since the first and second SAPs distributed onto the sheet are covered with the pulp layer, the movement of the distributed first and second SAPs in the planar direction is further suppressed compared with a case where the first and second SAPs distributed onto the sheet are covered with a sheet of nonwoven fabric or the like. For this reason, the variation of distribution of the first and second SAPs is excellently maintained.

Preferably, in the first step, the first SAP and the second SAP having different performances are distributed.

In this case, according to the combination of the performances of the SAPs, the range in which the performance of the absorbent material can be modified is further broadened, so that the degree of freedom in performance design can be further increased.

Moreover, to solve the above-mentioned problem, the present invention provides an absorbent material manufacturing device structured as follows:

An absorbent material manufacturing device is provided with: (a) a first duct having a first opening, conveying pulverized pulp up to the first opening and discharging it through the first opening; (b) a drum having an outer peripheral surface with air permeability disposed facing the first opening, and rotating; (c) a first distribution device having a first distribution opening disposed facing the outer peripheral surface of the drum and discharging a first SAP through the first distribution opening; and (d) a second distribution device having a second distribution opening disposed facing the outer peripheral surface of the drum and discharging a second SAP through the second distribution opening. The absorbent material manufacturing device is structured as follows: On the outer peripheral surface of the rotating drum, the pulp discharged through the first opening of the first duct is suctioned in a predetermined pattern to form a pulp layer in which the pulp is fiber-laminated, and then, the first SAP discharged through the first distribution opening is distributed onto the pulp layer and the second SAP discharged through the second distribution opening is distributed onto the pulp layer. The first distribution device can control the discharge amount of the first SAP. The second distribution device can control the discharge amount of the second SAP.

The absorbent material manufacturing device having the above-described structure can manufacture an absorbent material including the pulp layer, the first SAP and the second SAP.

According to the above-described structure, by using the first and second distribution devices, the distribution amount of the first SAP and the distribution amount of the second SAP can be controlled. For this reason, by changing the combination of the performances and distribution amounts of the first SAP and the second SAP, the performance of the absorbent material can be variously modified. Moreover, by changing either one or both of the distribution amount of the first SAP and the distribution amount of the second SAP while moving the pulp layer relative to the first distribution opening and the second distribution opening, an absorbent material can be easily manufactured in which the densities of the SAPs differ in the direction of the relative movement of the pulp layer.

That is, by using a plurality of distribution devices that discharge different SAPs and making it possible to control the distribution amounts of the SAPs, the modifiable distribution pattern of the SAPs can be expanded compared with a case where a single distribution device is used. For this reason, the range is broadened of a specific part in which modification of the performance of the absorbent material such as increasing the absorption performance of the front part in the length direction in the central part in the width direction can be made, so that the degree of freedom in performance design is increased.

Preferably, the absorbent material manufacturing device is further provided with: (e) a guide roll that guides a sheet in such a manner that the sheet with air permeability is along the outer peripheral surface of the drum. The absorbent material manufacturing device is structured as follows: On the sheet being conveyed along the outer peripheral surface of the drum, the pulp is suctioned in the predetermined pattern to form the pulp layer.

In this case, the absorbent material including the sheet can be easily taken out from the outer peripheral surface of the drum.

Preferably, the absorbent material manufacturing device is further provided with (f) a second duct having a second opening disposed facing the outer peripheral surface of the drum, conveying pulverized pulp the same as or different from the above pulp up to the second opening and discharging it through the second opening. The absorbent material manufacturing device is structured as follows: On the pulp layer in which the first SAP and the second SAP are distributed, the pulp discharged through the second opening is suctioned in a pattern the same as or different from the predetermined pattern and fiber-laminated.

In this case, an absorbent material in which the SAP layer is disposed between the pulp layers can be manufactured.

Moreover, to solve the above-mentioned problem, the present invention provides an absorbent material manufacturing device structured as follows:

An absorbent material manufacturing device is provided with: (a) a drum having an outer peripheral surface with air permeability and rotating; (b) a guide roll that guides a sheet in such a manner that the sheet is along the outer peripheral surface of the drum; (c) a first distribution device having a first distribution opening disposed facing the outer peripheral surface of the drum and discharging a first SAP through the first distribution opening; (d) a second distribution device having a second distribution opening disposed facing the outer peripheral surface of the drum and discharging a second SAP through the second distribution opening; and (e) a second duct having a second opening, conveying pulverized pulp up to the second opening and discharging it through the second opening. The absorbent material manufacturing device is structured as follows: Onto the sheet being conveyed along the outer peripheral surface of the drum, the first SAP discharged through the first distribution opening is distributed and the second SAP discharged through the second distribution opening is distributed; then, onto the sheet where the first SAP and the second SAP are distributed, the pulp discharged through the second opening of the second duct is suctioned in a predetermined pattern to form a pulp layer in which the pulp is fiber-laminated. The first distribution device can control the discharge amount of the first SAP. The second distribution device can control the discharge amount of the second SAP.

According to the above-described structure, by using a plurality of distribution devices that discharge different SAPs and making it possible to control the distribution amounts of the SAPs, the modifiable distribution pattern of the SAPs is expanded compared with a case where a single distribution device is used. For this reason, the range is broadened in which modification of the performance of the absorbent material such as increasing the absorption performance of the front part in the length direction in the central part in the width direction can be made, so that the degree of freedom in performance design is increased.

Moreover, since the first and second SAPs distributed onto the sheet are covered with the pulp layer, the movement of the distributed first and second SAPs in the planar direction is further suppressed compared with a case where the first and second SAPs distributed onto the sheet are covered with a sheet of nonwoven fabric or the like. For this reason, the variation of distribution of the first and second SAPs is excellently maintained.

Effects of the Invention

According to the present invention, a modifiable distribution pattern of an SAP is expanded, and the range in which the performance of the absorbent material can be modified is broadened, so that the degree of freedom in performance design can be increased.

MODE FOR CARRYING OUT THE INVENTION

Hereinafter, embodiments of the present invention will be described with reference to the drawings.

<First embodiment> A method and device for manufacturing an absorbent material of a first embodiment will be described with reference to FIGS. 1 to 3.

Figure 1:
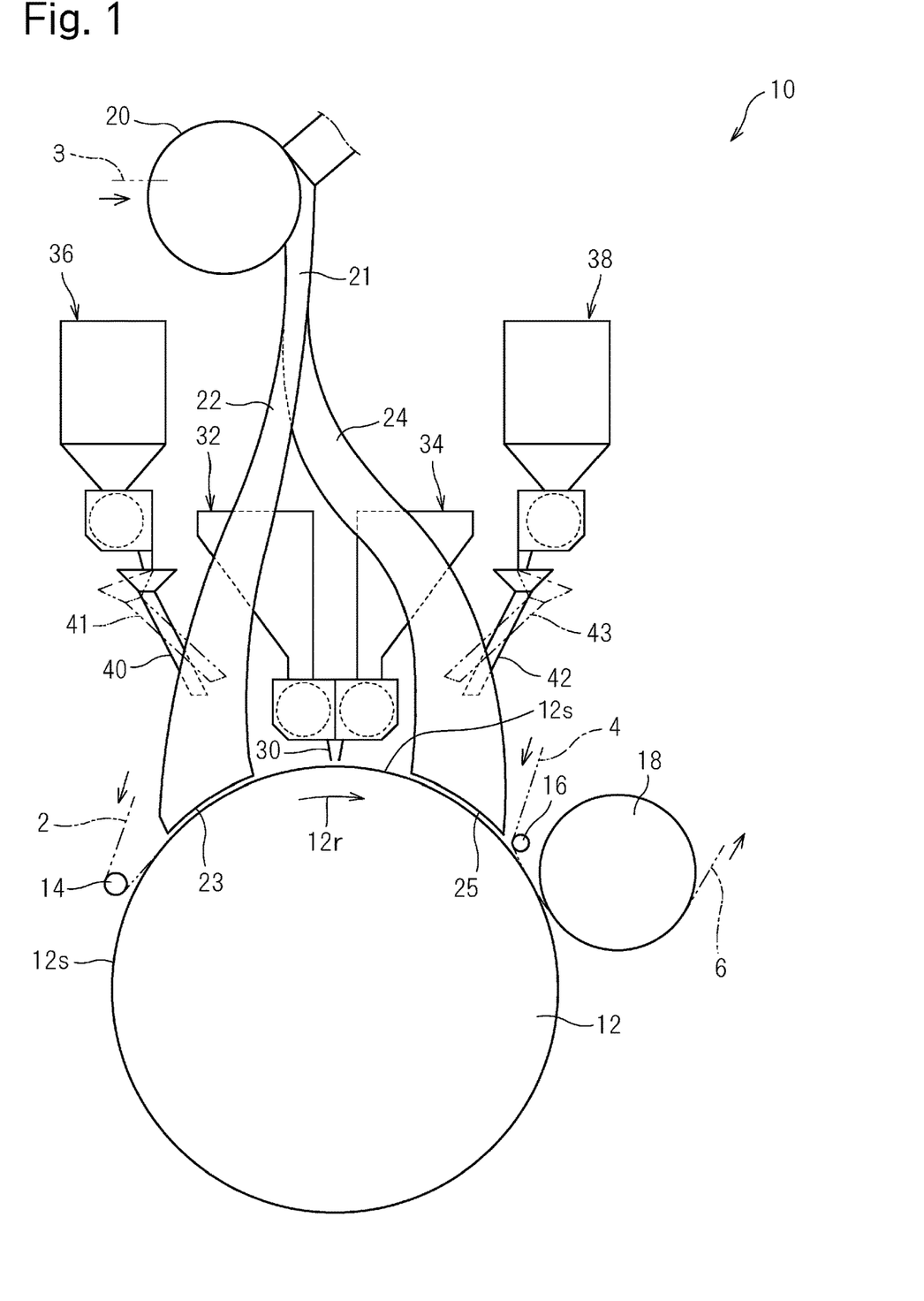
FIG. 1 is a general construction view of an absorbent material manufacturing device (first embodiment).

FIG. 1 is a general construction view of an absorbent material manufacturing device 10. As shown in FIG. 1, the absorbent material manufacturing device 10 is provided with a pulverization device 20, ducts 21, 22 and 24, a drum 12, a first distribution device 32 and a second distribution device 34.

The pulverization device 20 pulverizes sheet-like pulp 3. The pulp pulverized by the pulverization device 20 is conveyed by the ducts 21, 22 and 24. That is, the pulverized pulp is moved inside the ducts 21, 22 and 24. The ducts 21, 22 and 24 are such that the first duct 22 and the second duct 24 diverge from the main duct 21. The pulverized pulp is conveyed up to a first opening 23 of the first duct 22 and a second opening 25 of the second duct 24, and discharged through their respective openings 23 and 25.

A structure may be adopted in which the first and second ducts 22 and 24 are separated from the main duct 21, the first duct 22 conveys the pulp pulverized by a first pulverization device and the second duct 24 conveys the pulp pulverized by a second pulverization device. In this case, the materials of later-described pulp layers 7a and 7b may be different from each other.

Moreover, a structure may be adopted in which the second duct 24 is not provided and the pulverized pulp is discharged only through the first opening 23. In this case, an absorbent material not including the later-described pulp layer 7b can be manufactured.

The drum 12 has a cylindrical outer peripheral surface 12s and rotates. The outer peripheral surface 12s is disposed facing the first opening 23 of the first duct 22 and the second opening 25 of the second duct 24. The outer peripheral surface 12s has air permeability, and for example, a multiplicity of suction holes (not shown) are formed in a predetermined area of the outer peripheral surface 12s.

Figure 2:
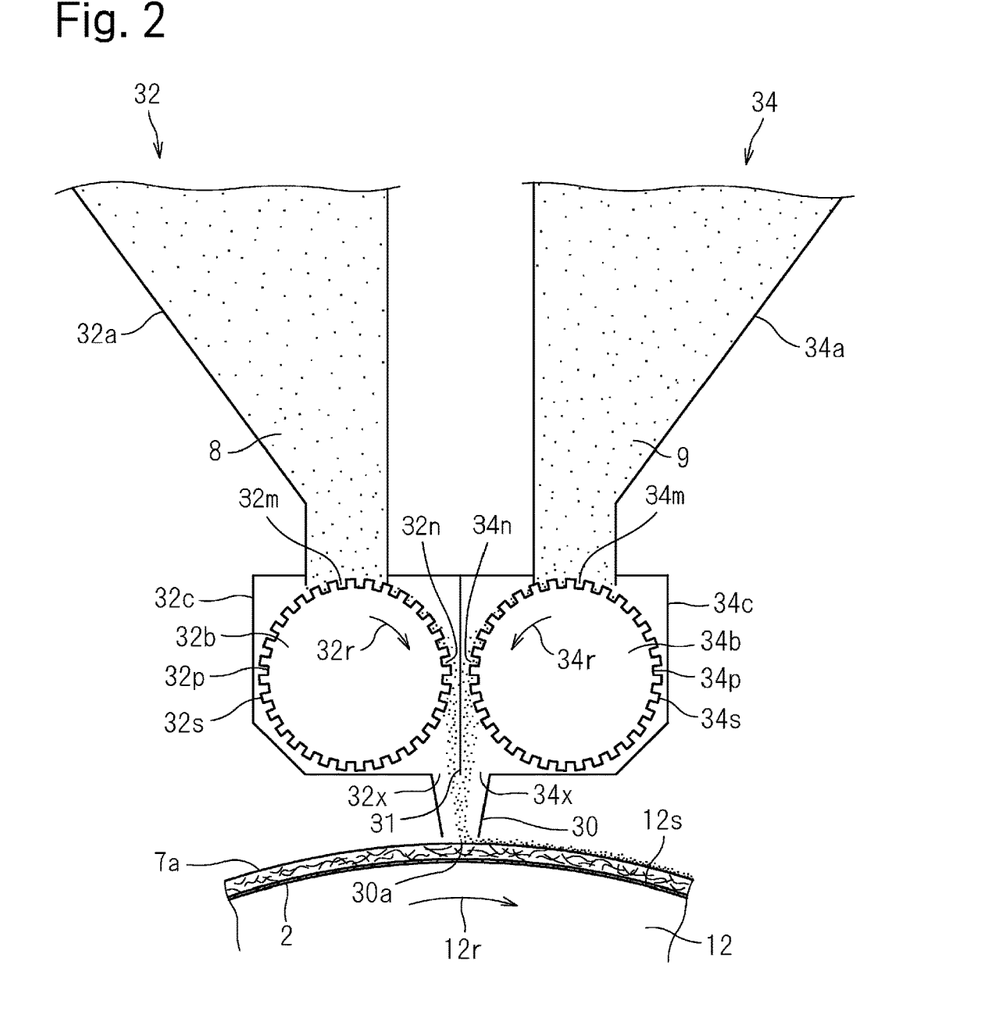
FIG. 2 is a relevant part cross-sectional view of the absorbent material manufacturing device (first embodiment).

FIG. 2 is a relevant part cross-sectional view of the absorbent material manufacturing device 10. As shown in FIG. 2, the first distribution device 32 and the second distribution device 34 are structured so as to be symmetrical. The first distribution device 32 has a first distribution opening 32x disposed facing the outer peripheral surface 12s of the drum 12, and discharges a first SAP 8 through the first distribution opening 32x. The second distribution device 34 has a second distribution opening 34x disposed facing the outer peripheral surface 12s of the drum 12, and discharges a second SAP 9 through the second distribution opening 34x.

Specifically, in the first and second distribution devices 32 and 34, casings 32c and 34c are coupled to the bottoms of hoppers 32a and 34a for storing the granular or powdery first and second SAPs 8 and 9, respectively. At the bottoms of the casings 32c and 34c, the first and second distribution openings 32x and 34x are formed.

Inside the casings 32c and 34c, rotors 32b and 43b are disposed. The rotors 32b and 34b have grooves 32p and 34p formed on outer peripheral surfaces 32s and 34s thereof. The size, shape, number, disposition and the like of the grooves 32p and 34p are chosen as appropriate. For example, a plurality of grooves 32p and 34p having the same size and shape and extending parallel to the center lines of rotation of the rotors 32b and 34b are formed at regular intervals in the circumferential direction of the rotors 32b and 34b.

The rotors 32b and 34b are disposed so that upper parts thereof face the lower openings of the hoppers 32a and 34a. The rotors 32b and 34b are structured so that the SAPs 8 and 9 drop from the grooves 32n and 34n when the SAPs 8 and 9 inside the hoppers 32a and 34a enter the grooves 32m and 34m situated on upper parts of the rotors 32b and 34b and the grooves 32m and 34m that the SAPs 8 and 9 have entered move approximately 90 degrees as the rotors 32b and 34b rotate in the directions indicated by the arrows 32r and 34r. The first and second distribution openings 32x and 34x are formed so that the first and second SAPs 8 and having dropped from the grooves 32n and 34n pass therethrough, respectively.

The first and second distribution devices 32 and 34 are structured so that they can control the number of rotations of the rotors 32b and 34b, respectively. The amounts of discharge of the first and second SAPs 8 and 9 through the first and second distribution openings 32x and 34x vary according to the numbers of rotations of the rotors 32b and 34b of the first and second distribution devices 32 and 34. Therefore, the first distribution device 32 can control the amount of discharge of the first SAP 8 through the first distribution opening 32x and the second distribution device 34 can control the amount of discharge of the second SAP 9 through the second distribution opening 34x.

Although not shown, the following may be performed: The distribution amount of the first and/or the second SAP 8 and/or 9 is detected on the downstream side of the first and second distribution openings 32x and 34x in the rotation direction of the drum 12 and based on the result, the discharge amount of the first and/or the second SAPs 8 and/or 9 is controlled. In this case, an absorbent material having a desired performance can be manufactured.

The first and second distribution openings 32x and 34x may have structures being different from each other in size and shape. For example, the widths of the first and second distribution openings 32x and 34x, that is, the sizes thereof in the direction parallel to the center line of rotation of the drum 12 may be different from each other. In this case, the widths of the distributed first and second SAPs 8 and 9 can be made different from each other.

When the rotors 32b and 34b rotate in the directions indicated by the arrows 32r and 34r, the first and second distribution openings 32x and 34x adjoin each other. In this case, a condition can be created in which the first and second SAPs 8 and 9 discharged through the first and second distribution openings 32x and 34x are mixed together.

A pair of guide plates 30 extending below the first and second casings 32c and 34c may be provided around the first and second distribution openings 32x and 34x. In this case, the distribution ranges of the first and second SAPs 8 and 9 can be limited to an area 30a (see FIG. 2) between the guide plates 30.

A structure may be adopted in which between the above-described adjoining first and second distribution openings 32x and 34x, a partition plate 31 (see FIG. 2) that separates them from each other is provided and the lower end of this partition plate 31 is extended to the neighborhood of the lower ends of the above-described guide plates 30. Alternatively, the rotation directions of the first and second rotors 32b and 34b may be other than the directions indicated by the arrows 32r and 34r. In these cases, the first and second distribution openings 32x and 34x are separated from each other, which makes it possible for the first and second SAPs 8 and 9 to be separately distributed through the distribution openings 32x and 34x, respectively, without being mixed together.

The first distribution device 32 and the second distribution device 34 may be structured so as not to be plane-symmetrical. The first distribution device 32 and the second distribution device 34 may have either the same structure or different structures.

Although not shown, inside the drum 12, suction chambers for sucking air from the outside toward the inside of the drum 12 are provided in positions facing the first opening 23, the second opening 25 and the first and second distribution openings 32x and 34x, respectively.

As shown in FIG. 1, the absorbent material manufacturing device 10 is further provided with: a first guide roll 14 that guides a first sheet 2; a second guide roll 16 that guides a second sheet 4; and a third guide roll 18 that guides the manufactured absorbent material 6 on the outer peripheral surface 12s of the drum 12.

Figure 3:
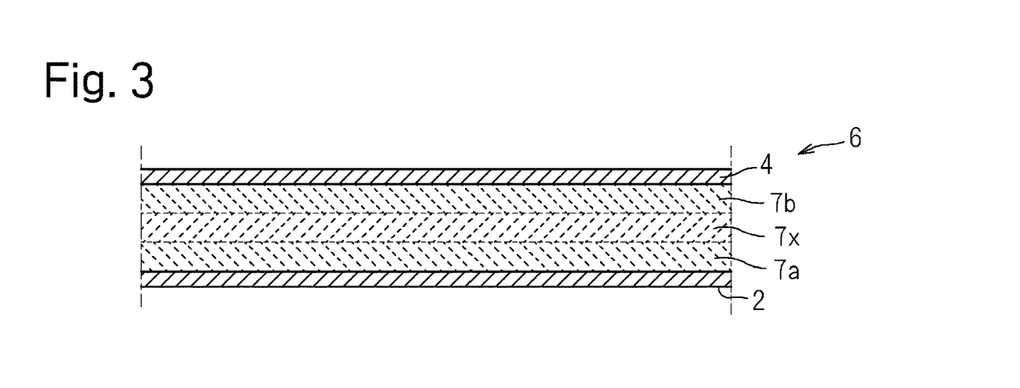
FIG. 3 is a cross-sectional view of an absorbent material (first embodiment).

FIG. 3 is a cross-sectional view of the absorbent material 6 manufactured by using the absorbent material manufacturing device 10. As shown in FIG. 3, in the absorbent material 6, an SAP layer 7x in which the first SAP 8 and the second SAP 9 are mixed is sandwiched between the pulp layer 7a adjoining the first sheet 2 and the pulp layer 7b adjoining the second sheet 4.

As the first and second SAPs 8 and 9, SAPs having different performances may be used, and the distribution ratio therebetween is set as appropriate. By doing this, the performance of the absorbent material 6 can be variously modified. The performance of the SAP includes the liquid permeability, the absorption speed, the absorption amount and the like when the SAP swells. The performance of the SAP varies according to the ingredients, particle diameter, particle shape, granularity distribution and the like of the SAP.

Next, the operation of the absorbent material manufacturing device 10 will be described with reference to FIGS. 1 to 3.

The drum 12 rotates in the direction indicated by the arrow 12r in FIGS. 1 and 2. The air-permeable first sheet 2 is wound in a predetermined area of the outer peripheral surface 12s of the drum 12 through the first guide roll 14, and the first sheet 2 is conveyed with the rotation of the drum 12. The first sheet 2 successively faces the first opening 23 of the first duct 22, the first distribution opening 32x of the first distribution device 32, the second distribution opening 34x of the second distribution device 34 and the second opening 25 of the second duct 24.

Pulverized pulp is discharged through the first opening 23 of the first duct 22. The discharged pulp is suctioned in a predetermined pattern such as a continuous or intermittent belt-like form on the outer peripheral surface 12s side of the drum 12 and accumulates on the air-permeable first sheet 2 to form the pulp layer 7a on the first sheet 2.

The first and second distribution devices 32 and 34 discharge the first and second SAPs 8 and 9 through the first and second distribution openings 32x and 34x, respectively. The discharged first and second SAPs 8 and 9 are suctioned toward the drum 12 and distributed onto the pulp layer 7a to form the SAP layer 7x on the pulp layer 7a.

In a case where the first distribution opening 32x and the second distribution opening 34x adjoin each other, the first and second SAPs 8 and 9 are distributed in a state of being mixed together. For this reason, in the SAP layer 7x, the first SAP 8 and the second SAP 9 are mixed together in the direction of the thickness.

In a case where the first distribution opening 32x and the second distribution opening 34x are separated from each other, inside the SAP layer 7x, the density of the first SAP 8 is high on the side of the first sheet 2, and the density of the second SAP 9 is high on the side of the second sheet 4.

In this case, for example, the SAPs are distributed so that the SAP that is high in liquid permeability when it swells is disposed on the non-skin surface side of the absorbent material. Thereby, the performance of the absorbent material can be adjusted so that urine is diffused in the pulp layer on the non-skin surface side and urine is absorbed in a wide area of the absorbent material by transmitting urine to the non-skin surface side.

Pulverized pulp is discharged through the second opening 25 of the second duct 24. The discharged pulp is suctioned in a predetermined pattern such as a continuous or intermittent belt-like form on the outer peripheral surface 12s side of the drum 12 to form the pulp layer 7b on the SAP layer 7x.

The second guide roll 16 guides the second sheet 4 in such a manner that the first sheet 2 is overlapped by the second sheet 4 and the second sheet 4 covers the pulp layer 7b.

The third guide roll 18 guides the absorbent material 6 having the pulp layers 7a and 7b and the SAP layer 7x between the first sheet 2 and the second sheet 4, in a direction away from the outer peripheral surface 12s of the drum 12.

In a case where the SAPs are dispersed in the pulp layers 7a and 7b, as shown in FIG. 1, third and fourth distribution devices 36 and 38 are provided. The third and fourth distribution devices 36 and 38 can, like the first and second distribution devices 32 and 34, control the discharge amounts of the SAPs by the numbers of rotations of the rotors.

The third and fourth distribution devices 36 and 38 supply the SAPs to the base ends of first and second supply tubes 40 and 42 whose ends are inserted in the first and second ducts 22 and 24, respectively. The supplied SAPs are supplied into the first and second ducts 22 and 24 from the ends of the first and second supply tubes 40 and 42, and mixed with the pulverized pulp inside the first and second ducts 22 and 24. The first and second supply tubes 40 and 42 are movable as indicated by chain lines 41 and 43, respectively, so that the positions of the ends of the first and second supply tubes 40 and 42 can be adjusted.

Next, the method for manufacturing the absorbent material will be described.

(1) First, the pulp pulverized and conveyed by the duct is suctioned in a predetermined pattern to form a pulp layer in which the pulp is fiber-laminated. This is a first step.

Specifically, on the air-permeable first sheet 2 disposed along the outer peripheral surface 12s of the rotating drum 12, the pulp discharged through the first opening 23 of the first duct 22 is suctioned in a predetermined pattern to form the pulp layer 7a. Forming the pulp layer 7a on the first sheet 2 makes it easy to take out the absorbent material 6 including the first sheet 2 from the outer peripheral surface 12s of the drum 12.

In the first step, for example as in the conventional example, the pulp layer 7a may be directly formed in a predetermined area of the outer peripheral surface 12s of the rotating drum 12.

(2) Then, the first distribution opening through which the first distribution device discharges the first SAP and the second distribution opening through which the second distribution device discharges the second SAP are provided facing the pulp layer, and the first SAP discharged through the first distribution opening is distributed onto the pulp layer and the second SAP discharged through the second distribution opening is distributed onto the pulp layer while moving the pulp layer relative to the first distribution opening and the second distribution opening. This is a second step. In the second step, the first SAP and the second SAP having different performances are distributed, the first distribution device can control the discharge amount of the first SAP, and the second distribution device can control the discharge amount of the second SAP.

Specifically, when the pulp layer 7a that moves with the rotation of the drum 12 faces the first and second distribution openings 32x and 34x of the first and second distribution devices 32 and 34, the first and second SAPs 8 and 9 discharged through the first and second distribution openings 32x and 34x are distributed onto the pulp layer 7a. The first and second SAPs 8 and 9 have different performances. The first and second distribution devices 32 and 34 can control the discharge amounts of the first and second SAPs 8 and 9 by changing the number of rotations of the rotors 32b and 34b, respectively.

(3) Then, on the pulp layer in which the first SAP and the second SAP are distributed, pulverized pulp the same as or different from the pulp used for the formation of the pulp layer is suctioned in a pattern the same as or different from the predetermined pattern at the time of formation of the pulp layer in the first step and fiber-laminated. This is a third step. The third step may be omitted.

Specifically, on the pulp layer 7a in which the first and second SAPs 8 and 9 are distributed, the pulp discharged through the second opening 25 of the second duct 24 is suctioned in a pattern the same as or different from the predetermined pattern at the time of formation of the pulp layer 7a to form the pulp layer 7b.

(4) Then, the second sheet is overlaid on the first sheet and covers the pulp layer formed in the third step or the pulp layer in which the first and second SAPs are distributed in the second step. This is a fourth step. The fourth step may be omitted.

Specifically, the second sheet 4 is guided through the second guide roll 16, the second sheet 4 is overlaid on the first sheet 2, and the pulp layer 7b is covered with the second sheet 4.

By the above steps, an absorbent material can be manufactured.

As described above, the use of the first and second distribution devices 32 and 34 enables distribution of the first SAP 8 and the second SAP 9 having different performances, so that the distribution amount of the first SAP 9 and the distribution amount of the second SAP 9 can be controlled. For this reason, by changing the combination of the performances and distribution amounts of the first SAP 8 and the second SAP 9, the performance of the absorbent material 6 can be variously modified.

Moreover, by changing either one or both of the distribution amount of the first SAP 8 and the distribution amount of the second SAP 9 while moving the pulp layer 7a relative to the first and second distribution openings 32x and 34x, an absorbent material 6 can be easily manufactured in which the densities of the SAPs 8 and 9 differ in the direction of the relative movement of the pulp layer 7a. For example, an absorbent material can be easily manufactured in which the performance differs between the central part and the peripheral part in the relative movement direction. Moreover, by making the axial directions of the rotors 32b and 34b different between the first distribution device 32 and the second distribution device 34, an absorbent material can be easily manufactured in which the performance differs between the central part and the peripheral part in the direction orthogonal to the relative movement direction.

That is, by using a plurality of distribution devices 32 and 34 that discharge the different SAPs 8 and 9 and making it possible to control the distribution amounts of the SAPs 8 and 9, the modifiable distribution pattern of the SAPs can be expanded compared with a case where a single distribution device is used. For this reason, the range in which the performance of the absorbent material can be modified is broadened, so that the degree of freedom in performance design is increased.

Distribution may be performed by using SAPs 8 and 9 having performances different from each other. In this case, according to the combination of the performances of the SAPs 8 and 9, the range in which the performance of the absorbent material can be modified is further broadened, so that the degree of freedom in performance choice can be further increased.

Figure 4:
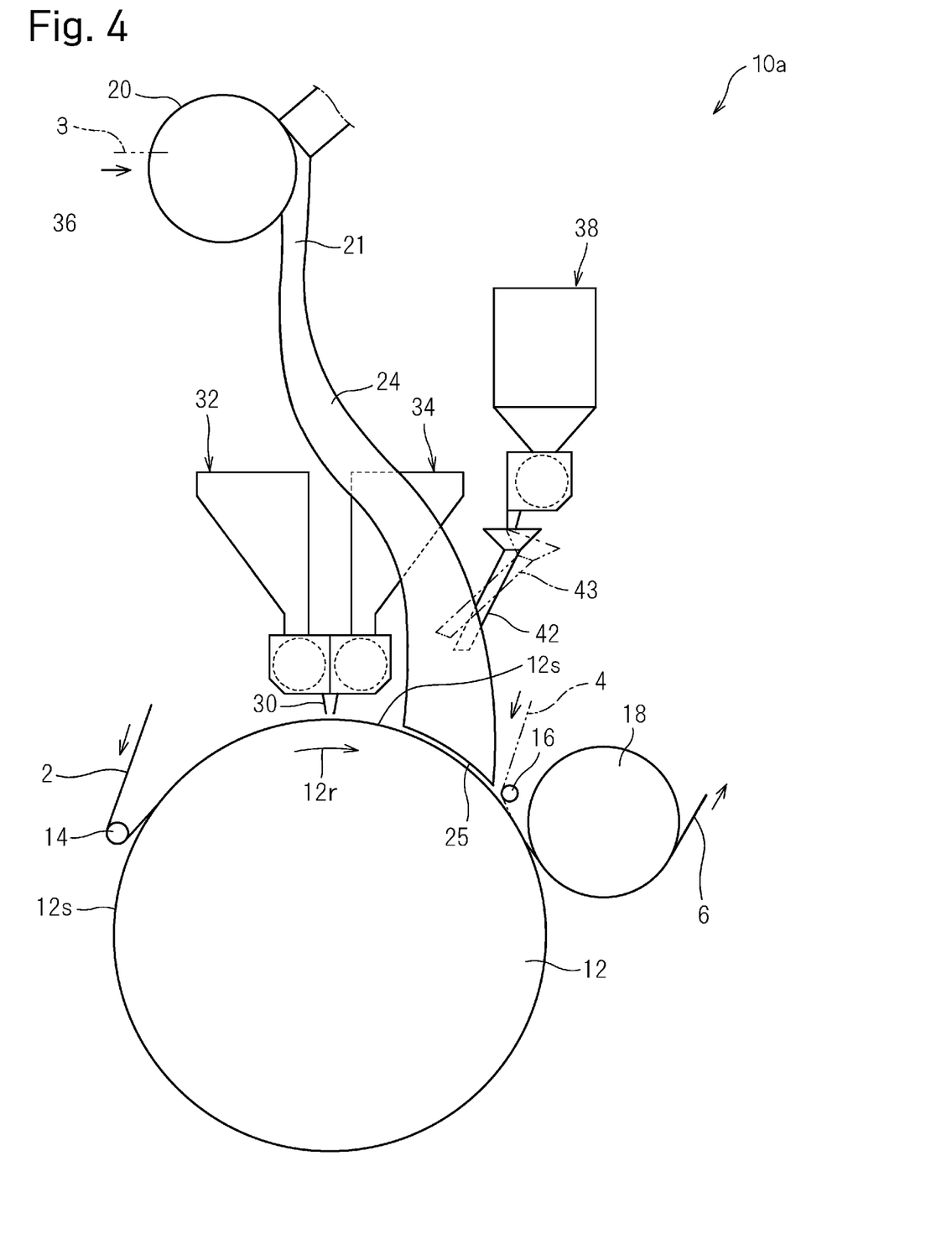
FIG. 4 is a general construction view of an absorbent material manufacturing device (second embodiment).
Figure 5:
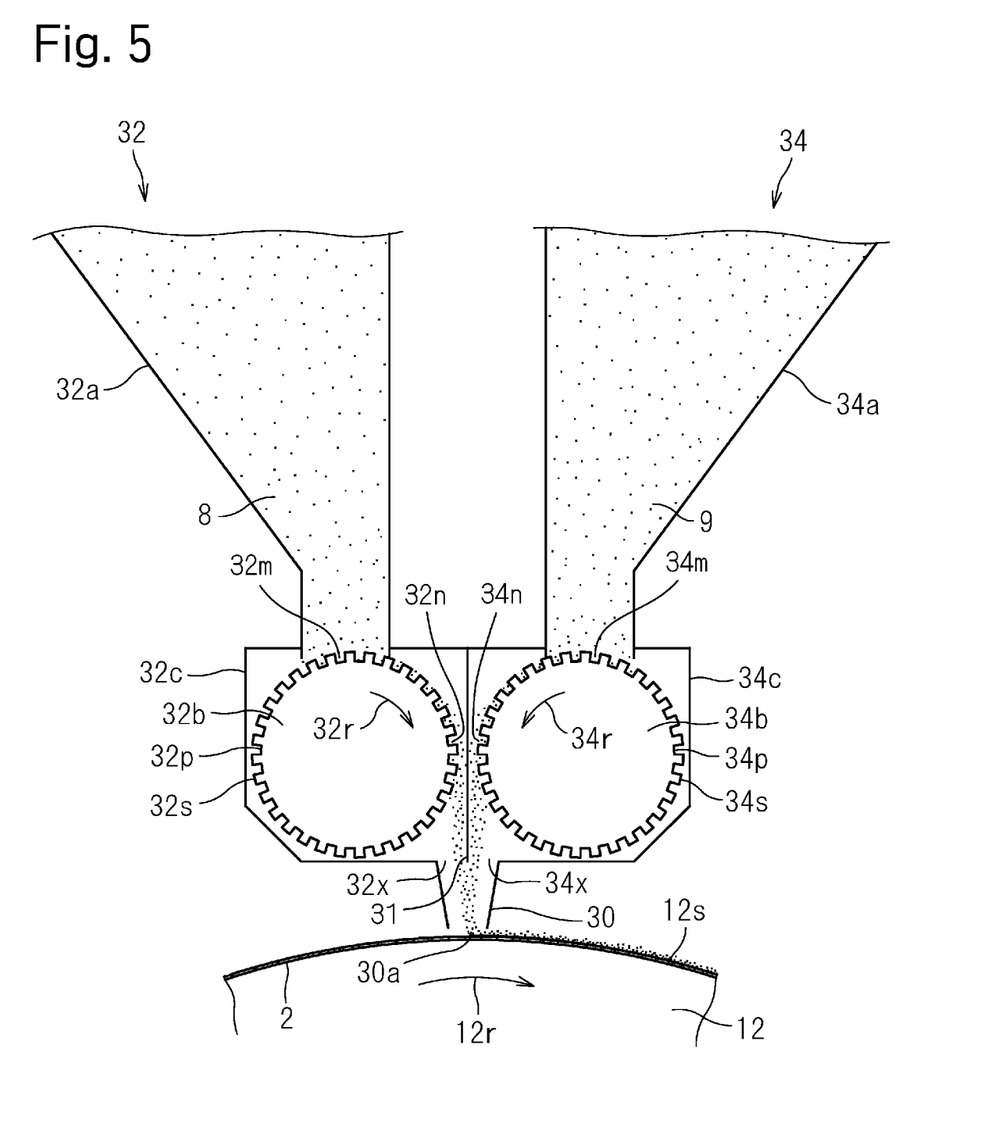
FIG. 5 is a relevant part cross-sectional view of the absorbent material manufacturing device (second embodiment).

<Second embodiment> A method and device for manufacturing an absorbent material of a second embodiment will be described with reference to FIGS. 4 and 5. FIG. 4 is a general construction view of an absorbent material manufacturing device 10a. FIG. 5 is a relevant part cross-sectional view of the absorbent material manufacturing device 10a. In the following, the same reference numerals are used for component parts similar to those of the first embodiment, and differences from the first embodiment will be mainly described.

As shown in FIGS. 4 and 5, although of the components of the absorbent material manufacturing device 10 of the first embodiment shown in FIGS. 1 and 2, the first duct 22 having the first opening 23 and the third distribution device 36 are not provided, except for this, the absorbent material manufacturing device 10a of the second embodiment is structured similarly to the absorbent material manufacturing device 10 of the first embodiment.

That is, the absorbent material manufacturing device 10a of the second embodiment is provided with: (a) the drum having the outer peripheral surface 12s with air permeability and rotating; (b) the guide roll 14 that guides the sheet 2 in such a manner that the sheet 2 is along the outer peripheral surface 12s of the drum 12; (c) the first distribution device 32 having the first distribution opening 32x disposed facing the outer peripheral surface 12s of the drum 12 and discharging the first SAP 8 through the first distribution opening 32x; (d) the second distribution device having the second distribution opening 34x disposed facing the outer peripheral surface 12s of the drum 12 and discharging the second SAP 9 through the second distribution opening 34x; and (e) the second duct 24 having the second opening 25, conveying pulverized pulp up to the second opening 25 and discharging it through the second opening 25. The absorbent material manufacturing device of the second embodiment is structured as follows: Onto the sheet 2 being conveyed along the outer peripheral surface 12s of the drum 12, the first SAP 8 discharged through the first distribution opening 32x is distributed and the second SAP 9 discharged through the second distribution opening 34x is distributed; then, onto the sheet 2 where the first SAP 8 and the second SAP 9 are distributed, the pulp discharged through the second opening 25 of the second duct 24 is suctioned in a predetermined pattern to form a pulp layer in which the pulp is fiber-laminated. The first distribution device 32 can control the discharge amount of the first SAP 8. The second distribution device 34 can control the discharge amount of the second SAP 9.

Next, the method for manufacturing the absorbent material of the second embodiment will be described.

(1) First, the first distribution opening 32x through which the first distribution device 32 discharges the first SAP 8 and the second distribution opening 34x through which the second distribution device 34 discharges the second SAP 9 are provided facing the sheet 2, and the first SAP 8 discharged through the first distribution opening 32x is distributed onto the sheet 2 and the second SAP 9 discharged through the second distribution opening 34x is distributed onto the sheet 2 while moving the sheet 2 relative to the first distribution opening 32x and the second distribution opening 34x. The first distribution device 32 can control the discharge amount of the first SAP 8, and the second distribution device 34 can control the discharge amount of the second SAP 9. This is a first step.

(2) Then, onto the sheet 2 where the first SAP 8 and the second SAP 9 are distributed, the pulp pulverized and conveyed by the second duct 24 is suctioned in a predetermined pattern to form a pulp layer, in which the pulp is fiber-laminated, so that the pulp layer covers the first SAP 8 and the second SAP 9 distributed onto the sheet 2. This is a second step.

When an absorbent material is manufactured by the above-described first and second steps, by using a plurality of distribution devices that discharge different SAPs and making it possible to control the distribution amounts of the SAPs, the modifiable distribution pattern of the SAP is expanded compared with a case where a single distribution device is used. For this reason, the range in which the performance of the absorbent material can be modified is broadened, so that the degree of freedom in performance design is increased.

Moreover, since the first and second SAPs distributed onto the sheet 2 are covered with the pulp layer, the movement of the distributed first and second SAPs in the planar direction is further suppressed compared with a case where the first and second SAPs distributed onto the sheet 2 are covered with a sheet of nonwoven fabric or the like. For this reason, the variation of distribution of the first and second SAPs is excellently maintained.

The sheet 2 may be any through which neither the first nor the second SAP passes, and the thickness thereof is not specifically limited. However, in a case where the sheet 2 is disposed on the skin side, a bulky sheet of air-through nonwoven fabric or the like is desirably used because it is soft.

In the first step, the first SAP 8 and the second SAP 9 having different performances may be distributed. In this case, according to the combination of the performances of the first and second SAPs 8 and 9, the range in which the performance of the absorbent material can be modified is further broadened, so that the degree of freedom in performance choice can be further increased.

After the pulp layer is formed in the second step, as in the method described in the first embodiment, the second sheet 4 may be guided through the second guide roll 16 to cover the pulp layer with the second sheet 4. Alternatively, the following may be performed: After the first and second SAPs are distributed except for an end portion of the sheet 2 in the width direction and the pulp layer is formed, the end portion of the sheet 2 in the width direction is folded back and placed on the pulp layer.

<Summary> As described above, the modifiable distribution pattern of the SAP is expanded and the range in which the performance of the absorbent material can be modified is broadened, so that the degree of freedom in performance design can be increased.

The present invention is not limited to the above-described embodiments and may be variously modified when carried out.

For example, while a case where two distribution devices are used is shown as an example, three or more distribution devices may be used. The larger the number of distribution devices is, the more various absorbent materials can be manufactured, so that the range in which the performance of the absorbent material can be modified can be further broadened.

Moreover, while a case where the pulp is fiber-laminated on the outer peripheral surface of the drum is shown as an example, the present invention is not limited thereto. For example, the pulp may be fiber-laminated on an endless belt having air permeability.

DESCRIPTION OF REFERENCE NUMERALS

2 First sheet (sheet)
6 Absorbent material
7a, 7b Pulp layer
10, 10a Absorbent material manufacturing device
12 Drum
12s Outer peripheral surface
14 First guide roll (guide roll)
22 First duct
23 First opening
24 Second duct
25 Second opening
32 First distribution device
32x First distribution opening
34 Second distribution device
34x Second distribution opening

The invention claimed is:

1. An absorbent material manufacturing device comprising:
  a first duct having a first opening, for conveying pulverized pulp up to the first opening and discharging the pulverized pulp through the first opening;
  a drum having an outer peripheral surface with air permeability disposed to face the first opening, and rotating;
  a first distribution device having a first distribution opening disposed outside the first duct on a downstream side of the drum in a rotating direction of the drum from the first opening of the first duct to face the outer peripheral surface of the drum, and discharging a first super absorbent polymer through the first distribution opening; and
  a second distribution device having a second distribution opening disposed outside the first duct on the downstream side of the drum in the rotating direction of the drum from the first opening of the first duct to face the outer peripheral surface of the drum, and discharging a second super absorbent polymer through the second distribution opening,
  wherein on the outer peripheral surface of the rotating drum, the pulp discharged through the first opening of the first duct is suctioned in a predetermined pattern to form a pulp layer in which the pulp is fiber-laminated, and then, the first super absorbent polymer discharged through the first distribution opening is distributed onto the pulp layer and the second super absorbent polymer discharged through the second distribution opening is distributed onto the pulp layer, and
  the first distribution device can control a discharge amount of the first super absorbent polymer, and the second distribution device can control a discharge amount of the second super absorbent polymer.

2. The absorbent material manufacturing device according to claim 1, further comprising a guide roll that is disposed along the outer peripheral surface of the drum on an upstream side of the drum in the rotating direction of the drum from the first opening of the first duct and guides a sheet in such a manner that the sheet with air permeability is disposed along the outer peripheral surface of the drum,
  on the sheet being conveyed along the outer peripheral surface of the drum, the pulp is suctioned in the predetermined pattern to form the pulp layer.

3. The absorbent material manufacturing device according to claim 1, further comprising a second duct having a second opening disposed on the downstream side of the drum in the rotating direction of the drum from the first distribution opening of the first distribution device and the second distribution opening of the second distribution device to face the outer peripheral surface of the drum, conveying pulverized pulp same as or different from the above pulp up to the second opening and discharging the pulverized pulp through the second opening,
  wherein on the pulp layer in which the first super absorbent polymer and the second super absorbent polymer are distributed, the pulp discharged through the second opening is suctioned in a pattern same as or different from the predetermined pattern and fiber-laminated.

4. The absorbent material manufacturing device according to claim 3, further comprising a third distribution device for supplying the first super absorbent polymer to the pulverized pulp into the first duct, and a fourth distribution device for supplying the second super absorbent polymer into the pulverized pulp in the second duct.

5. The absorbent material manufacturing device according to claim 4, wherein the third distribution device includes a first supply tube movably arranged in the first duct, and the fourth distribution device includes a second supply tube movably arranged in the second duct.

* * * * *